United States Patent [19]

Butera

[11] 4,214,480

[45] Jul. 29, 1980

[54] INTEGRATED SMOKE TESTER

[76] Inventor: Anthony W. Butera, 112 Tuthill St., Port Jefferson, N.Y. 11777

[21] Appl. No.: 941,956

[22] Filed: Sep. 13, 1978

[51] Int. Cl.² .............................................. G01N 1/24
[52] U.S. Cl. .............................................. 73/421.5 A
[58] Field of Search .......................... 73/421.5 A, 28

[56] References Cited

U.S. PATENT DOCUMENTS

| | | | |
|---|---|---|---|
| 3,464,257 | 9/1969 | Schreiber et al. | 73/28 |
| 4,095,729 | 6/1978 | Butera | 225/42 |

OTHER PUBLICATIONS

Burkhardt, Charles H. *Domestic and Commercial Oil Burners*, 1961, pp. 275-277.

*Primary Examiner*—Anthony V. Ciarlante

[57] ABSTRACT

This invention relates to an "Integrated Smoke Tester", a device for use in the sampling and smoke spot testing of the flue gases of an oil burner and consists of a sampling tube, a hand vacuum pump, valves, built-in storage filter paper dispenser, a knurled screw press pad and a paper severing feature. Said invention is to be used with roll strip material such as described in "Calibrated Oil Burner Filter Paper", U.S. Pat. No. 4,170,127 and provides a system for obtaining a paper record of the soot content and Smoke Spot Number of the flue gases of an oil burner.

5 Claims, 3 Drawing Figures

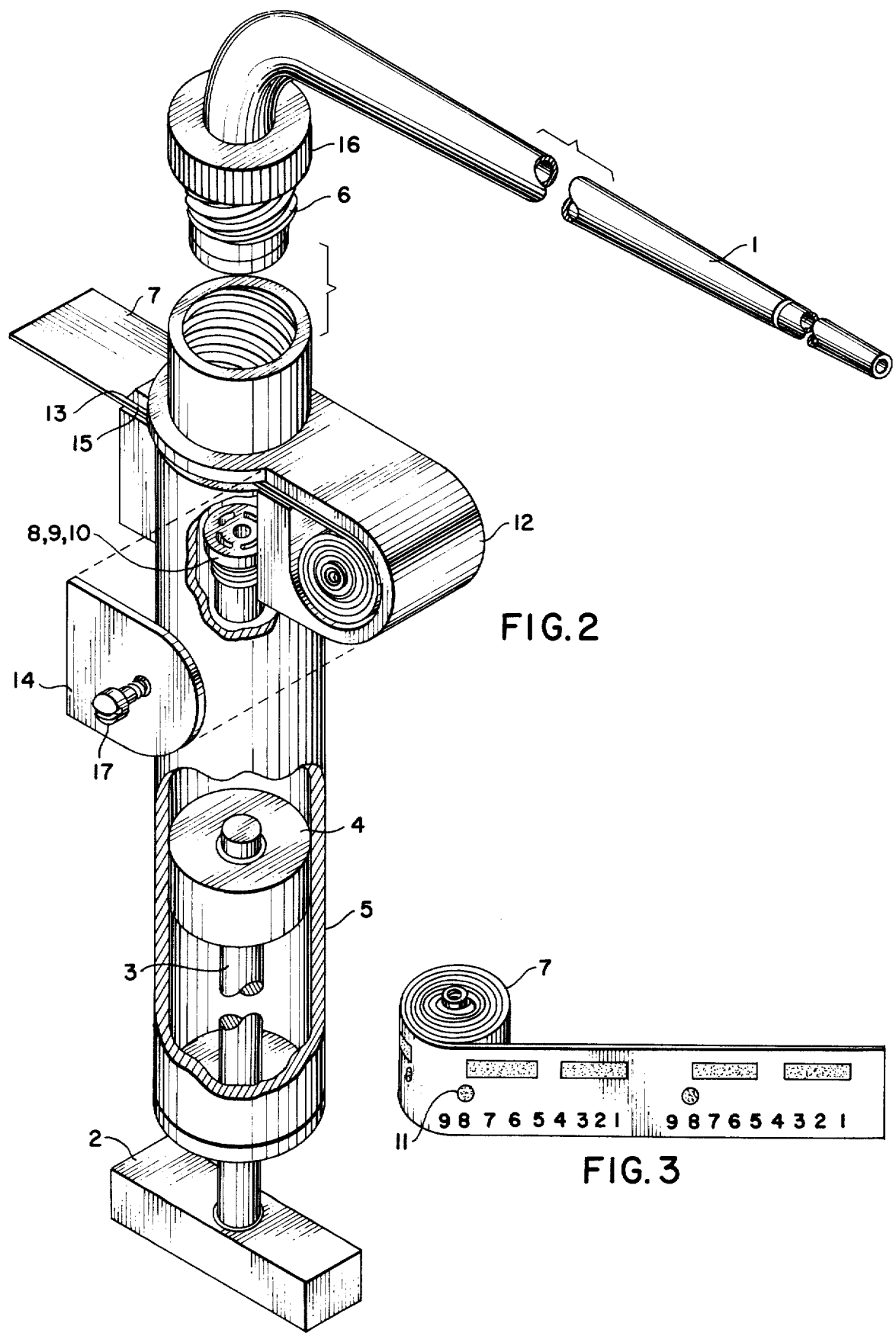

INTEGRATED SMOKE TESTER

BACKGROUND

Particular difficulty has been found in the present method of smoke spot testing the smoke content in the flue pipe of an oil burner, and in determing the Smoke Spot Number. Namely, the filter paper in common use today is in strip form and is obtained by the technician tearing off a useable piece of paper from a serrated sheet to form a useable strip. Herein lies one of the difficulties. Usually the technician making the test has either serviced the oil burner or has made an inspection. As a result his hands are quite often covered by a quantity of soot, oil, dust, or other matter generally found around an oil burner. Hence, the moment he selects a filter strip he imparts a print or smudge from his hands onto the filter paper even before he makes a test. This contamination can degrade the test data and lead to an erroneous conclusion. Also, the concept of placing a small strip of limp paper in a narrow slot is awkward and difficult and often falls out of the tester and on the floor where it is further dirtied.

Another difficulty of importance is that after a smoke spot test has been made, the test strip of filter paper must be removed from the spot tester and physically placed next to a standard smoke scale for inspection. In so doing, the test paper has to be handled again and can be easily smudged or dropped, further contamination resulting. Since several tests are usually made on one strip, any disorientation of the test strip by being dropped can cause confusion as to which was the first or the last test.

SUMMARY

A Filter Paper Dispenser U.S. Pat. No. 4,095,729 filing date June 20, 1978 and Calibrated Oil Burner Paper serial No. 890784 filing date Mar. 27, 1978 are two concepts to improve the aforementioned procedure to determine the smoke content of an oil burner flue gases.

An object of this invention is to incorporate into one tester the advantages and features of the aforementioned Patent and Patent application. Namely that the pump body and paper dispenser, clamping device, and severing device be integral and form a total combined unit.

A further object of the invention is to provide a unit that in combination with said pump and dispensing medium will facilitate the incremental movement for roll material in claibrated lengths as determined by the tests being performed.

Another object of the invention is to provide a paper dispenser and roll of strip material in such proximity with an air passage and Knurled screw press pad, or a clamping device that a sample smoke test can easily be obtained and the sample test can be severed from the stored roll without said roll being removed or being contaminated. The filter paper can be severed by a tearing action after the paper is clamped against the cutting edge with a finger of the testers hand. A more enumerative discussion of the objective of the invention, as applicable to the said device wherein the filter paper is unreeled from said dispenser and is re-located in a step by step procedure through a slot means, is that the said filter paper moves in the vicinity of a clamping assembly and is thus confined perpendicular to the axis of the pump housing between the sealing surface of a stationary check valve assembly, and a parallel moveable sealing surface of said knurled screw press pad, wherby said press pad bearing down upon the filter tape during the smoke spot test phase inhibits leakage losses during the smoke test phase.

Also taking into consideration other concepts which will be found in the following description the novelty of the invention is applicable in combination and order of parts as appears in the context and claims of this document.

BRIEF DESCRIPTION OF THE DRAWINGS

FIG. 2 is an isometric perspective and cutaway view of the device and illustrates the parts of the invention and in general covers the pump housing, valves, filter paper housing, filter paper, and probe respectively. The dispenser housing shown in thereof integral with the pump housing and is of one piece unit construction with said pump housing.

FIG. 3 is an isometric perspective of a Calibrated Filter Paper and appears as an example of one of the plurality of geometric forms as appears in U.S. Pat. No. 4,170,127.

DISCUSSION

Figure 1:
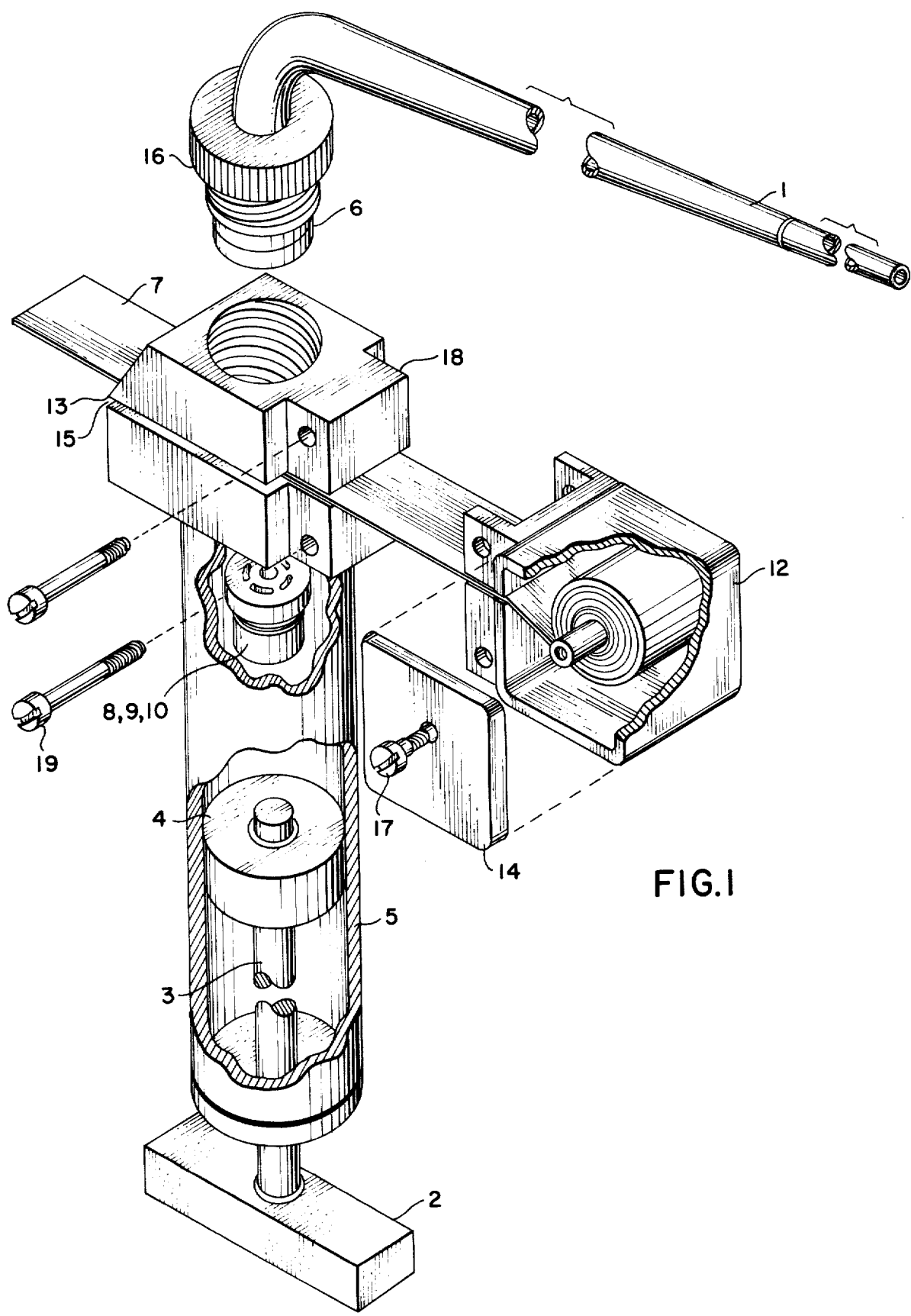
FIG. 1 is an isometric perspective and cutaway view of the device and illustrates the parts of the invention and in general covers the pump housing, valves, filter paper housing, filter paper and probe respectively. The filter paper housing is shown detached from the mount flange to illustrate that the said filter paper housing is an attachment to the integral mount flange of the pump housing.

These features can be more clearly understood when considered in conjunction with the accompanied drawings, sheet 1 and 2, FIGS. (1), (2) and (3). In FIG. (1) the sequence of operation consists mainly of clamping in place the filter paper (7) inserting the smoke sampling tube (1) into an oil burner smoke pipe and filtering a prescribed quantity of flue gas through the filter paper (7) and smoke tester by stroking the handle (2) a prescribed number of times. The action is such that by pulling the pump handle (2), pump shaft (3) and pump plunger (4), in the pump housing (5) a vacuum is created and a sample of flue gas is drawn thru the tube (1), the trap (6), filter paper (7), check valve assembly (8), (including valve flap(9) ), condensate trap (10) and into the cylinder chamber of the housing (5). The action of the valve flap (9) is to prohibit the flue gas from being forced through the filter paper (7). By pulling the handle (2) a number of times consistent with a calibration schedule peculiar to each tester, and calibrated filter paper a predetermined volume of gas will be filtered through the paper (7) and a deposit of soot (11), will be left on the filter paper (7). This deposit of soot when compared with a calibrated smoke scale such as defined in U.S. Pat. app. No. 890,784, is the basis of determining the Smoke Spot Number or the degree of unburned carbon and is instrumental in determining the burning efficiency of an oil burner. The filter paper (7) is housed in a configuration which can have a filter paper housing such as (12) and cover (14) attached with screws (19) to a built in integral flange (18) on the pump housing (5). The housing (12) is loaded with filter paper (7) by removing the cover screw (17) and cover (14) and inserting a predetermined roll of filter paper (7) into the bore of the housing (12) and putting the cover (14) back in place in the filter paper housing (12). The paper (7) is then fed through a slot traversing the housing (15), pump housing (5) and across the serrated cutting edge (13). The cover (14) is then secured by assembly with cover screw (17). The paper (7) is then pulled through the slot (15) in position for test and locked in place by tightening the knurled screw press pad (16). FIG. 2, sheet 2 of 2 depects another version whose function is identical to the aforementioned unit. FIG. 1 sheet 1 of 2, however; illustrates the filter paper housing (12) as an integral (as cast) part of the pump housing (5). The innovation is that the body of the smoke tester (5) and the dispenser (12) and the clamping action of Knurled screw press pad (16) in combination and arrangement of parts thereof form one integral unit.

Although drawings FIG. (1) and FIG. (2) show two preferred forms of the invention, it is to be understood that other embodiments and configurations arising out of production economics or otherwise and incorparating the elements of a pump, method of attachment, valves, sealing surfaces, clamping devices shafts, plungers, probes, flanges, screws, materials, etc., may be made which come within the scope and essence of the claims.

Furthermore, the filter paper is positioned and is typical in operation to that as explained in U.S. Pat. App. No. 890,784, and when housed in a dispenser such as (12) is fed through slot (15) of the mount flange (18). The filter paper is held in place by tightening the knurled screw press pad (16) and after a test, is removed by loosening said knurled screw and tearing the paper against the cutting edge (13). The paper is now the position for the next test.

Although the drawings, FIGS. 1, 2 and 3 show several preferred forms of the invention, it is to be understood that other embodiments may be made which come within the scope and essence of the claims.

I claim:

1. An integrated smoke tester for use in sampling and testing the smoke of flue gasses of an oil burner and for determining the smoke content and smoke spot number of said flue gasses by withdrawing a predetermined sample of flue gasses from an oil burner flue pipe with said tester comprising: a sampling test probe, a hand operated vacuum pump containing a longitudinal bore housing and a valve, a built-in test strip material dispenser and cover for containing a roll of strip material for rotation about an axis, said dispenser being attached to a slotted housing attached to said pump housing and containing a cutting edge, a clamping assembly for securing said strip material between a sealing surface of said slotted housing and a parallel movable sealing surface of said clamping device, the rotational axis of said roll being located laterally and perpendicular to the longitudinal axis of the bore of said pump, said dispenser containing a slot located adjacent said slot in said slotted housing whereby a continuous slot is provided running from the dispenser, between the surface of said clamping assembly and sealing surface of said slotted housing to the cutting edge of said slotted housing, said cutting edge being perpendicular to said bore axis and spaced laterally and at the extremity of said slot at an opposite end of said slotted housing from said dispenser.

2. The tester of claim 1 wherein finger accomodating space is provided between said serrated cutting edge and pump housing so that the user can grasp an emerging end portion of the roll strip material for step by step manual withdrawal of increments of strip material.

3. The tester of claim 1 wherein finger accomodating space is provided between said clamping assembly and the dispenser.

4. The tester of claim 1 wherein said slotted housing is integral with said pump housing, said cutting edge is serrated and said dispenser is detachable from said slotted housing.

5. The tester of claim 1 wherein the slotted housing, pump housing and dispenser form a one piece unit construction.

* * * * *